United States Patent [19]
Lajiness-O'Neill

[11] Patent Number: 5,203,763
[45] Date of Patent: Apr. 20, 1993

[54] DYNAMIC SLING

[76] Inventor: Renée Lajiness-O'Neill, 4061 W. 5580 S., Kearns, Utah 84118-4444

[21] Appl. No.: 830,653

[22] Filed: Feb. 4, 1992

[51] Int. Cl.$^5$ ............................................... A61F 5/00
[52] U.S. Cl. .......................................... 602/4; 602/20
[58] Field of Search ................... 602/4, 20, 21, 26, 62, 602/63; 128/869–876; 2/216, 305, 311, 312; 111/96, 101, 109, 126

[56] References Cited

U.S. PATENT DOCUMENTS

| | | | |
|---|---|---|---|
| 1,808,422 | 6/1931 | MacDonald | 602/4 |
| 2,460,589 | 2/1949 | Lewis | 602/4 |
| 3,404,680 | 10/1968 | Gutman | 602/4 |
| 3,515,131 | 6/1970 | Stevens | 602/4 |
| 3,906,944 | 9/1975 | Christen | 128/869 |
| 4,598,703 | 7/1986 | Lindemann | 602/4 |
| 4,763,901 | 8/1988 | Richter | 602/20 |
| 4,844,306 | 7/1989 | Ruff | 602/4 |
| 4,875,677 | 10/1989 | Tetreault | 602/20 |
| 4,896,660 | 1/1990 | Scott | 602/20 |

FOREIGN PATENT DOCUMENTS 0190631 7/1957 Fed. Rep. of Germany ... 128/DIG. 19

*Primary Examiner*—Robert A. Hafer
*Assistant Examiner*—Michael Brown
*Attorney, Agent, or Firm*—Basile and Hanlon

[57] ABSTRACT

A dynamic sling provides a patient with therapeutic movement including joint approximation and proprioceptive input for an affected extremity joint, such as an arm and shoulder joint. The dynamic sling includes a first cuff for attachment to a patient's non-affected arm adjacent, or spaced from the shoulder along the humerus between the elbow joint and the shoulder joint. A second cuff is provided for attachment to the patient's affected arm adjacent the affected joint or spaced from the joint along the humerus between the elbow joint and the shoulder joint. An attachment member connects the first and second cuffs to one another crossing over the shoulder adjacent the affected joint. The attachment member connects adjacent to the rear of the non-affected arm and connects adjacent to the front of the affected arm. A guide member guides a portion of the attachment member between the first and second cuffs at a location generally contiguous with the cross over area of the attachment member over the shoulder of the affected arm to protect the patient against abrasions and bruising that may be caused by movement of the attachment member while transferring motion from the non-affected arm to the affected arm.

19 Claims, 1 Drawing Sheet

DYNAMIC SLING

FIELD OF THE INVENTION

The dynamic sling of the present invention relates to an orthotic device to promote glenohumeral joint integrity, normalization of muscular tone, and movement for patients with hemiparesis and hemiplegia following central nervous system dysfunction.

BACKGROUND OF THE INVENTION

Shoulders are the most movable, and one of the most fragile, joints in the human body. A shoulder has a range of motion that no other joint in the body comes even close to matching. It is the shoulder's flexibility that enables the arms to be useful in a variety of activities. By moving the arm into a wide variety of positions, the shoulder multiplies the arm is usefulness. Although the shoulder is an excellent positioner for the arm, it is not a good anchor. The shoulder's flexibility makes it prone to sudden injury and chronic wear and tear. Often someone with pain in the arm, hand, or neck may have trouble moving the shoulder. Likewise, shoulder pain can affect arm and hand movement. It is natural to react to shoulder pain by not moving the shoulder, which can result in almost total loss of the ability to move the shoulder at all. Fortunately a doctor, sometimes with the aid of a physical therapist or occupational therapist, can almost always treat shoulder problems successfully, particularly if the patient follows a recommended exercise program designed to keep the shoulder in motion.

The shoulder is a complex arrangement of three bones held together by muscles, tendons, and ligaments. The clavicle, or collar bone, attaches the shoulder to the rib cage and holds the shoulder out from the trunk of the body. The clavicle connects with the large, flat, triangular scapula, or shoulder blade, at the acromion. The acromion projects from the scapula to form the top of the shoulder. The acromion in combination with the coracoid, also part of the scapula, and attaching ligaments form a socket called the glenoid fossa. The ball-like head of the humerus, or upper arm bone, is cradled in the glenoid fossa forming the glenohumeral joint, better known as the shoulder joint. The shallow ball-and-socket joint formed by the glenohumeral joint is held together by a group of tendons, known as the rotator cuff, that attach to the chest and back muscles. The bicep's tendons run out of the shoulder joint and down to the upper arm muscle. Between the acromion and the rotator cuff lies a bursa that cushions the tendon from the bone. The bursa is a small sack filled with fluid, generally the consistency of motor oil. The shoulder can move the arm around in a full circle, as well as back and forth, and up and down. Much of this motion is due to three joints in the shoulder, that serve to orient the shoulder joint itself in a given direction. One of these joints is the acromioclavicular joint. The acromioclavicular joint acts as a hinge for raising the shoulder. The scapula and humerus also play important roles in allowing full motion of the shoulder.

Common medical terms for describing shoulder movements include flexion, extension, abduction, adduction, external rotation and internal rotation. Shoulder flexion is the movement of raising the arm straight in front of the body over the head. Extension is the movement of moving the arm straight behind the body. Abduction is the movement of raising the arm out to the side over the head while keeping the arm straight. Horizontal adduction is the movement of raising the arm to shoulder height and bringing the arm out to the side, then in front of the body and out to the side again. Internal rotation is the movement of having the elbow bent and against the side of the body and moving the forearm as close to the stomach as possible. External rotation is the movement of having the elbow bent and against the side of the body and moving the forearm and hand from a position close to the stomach out to the side of the body.

The shoulder is a very vulnerable joint which typically becomes dysfunctional following neurologic disease or trauma, such as a cerebral vascular accident (stroke) or traumatic brain injury. Following a stroke or head injury, patients frequently experience paralysis on one side of their body, referred to as hemiplegia. Prior to injury, the shoulder is one joint in our body which compromises stability for mobility. Following a stroke or head injury the already unstable joint looses the muscular stability that maintains the joint integrity. As a result, the head of the humerus drops out of the glenoid fossa, resulting in what is known as a sublexed shoulder or sublexation. Furthermore, due to the cortical damage, patients are frequently left with sensory impairments or substantial pain in this region.

Occupational therapists or physical therapists are the rehabilitation professionals who patients are referred to by their physicians to treat these motor and sensory deficits. Treatment typically consists of specific neurodevelopmental techniques to facilitate normalized muscle tone, increase range or motion, decrease pain, improve coordination and eventually strength. Before normal movement can be attained the motor and sensory dysfunction, as well as the pain at the shoulder joint must be treated. Typical treatment includes techniques such as weight bearing, joint approximation and proprioceptive input through the joint to increase muscular tone in order to decrease the joint separation (sublexation) and pain. Compensatory aids, such as static arm slings are sometimes used to help with positioning of the arm as rehabilitation progresses. However, these slings have not typically been therapeutic and are fraught with controversy as they place the arm in a bent and nonfunctional position. Furthermore, they typically facilitate spasticity, which is contraindicated for the hemiplegic arm.

While occupational and physical therapies are effective ways to treat symptoms of diseases, injuries, and disabilities of various types, it typically requires an extremely long period of time before the patient reaches full o significant partial recovery. In part, this may be due to the short period of time spent in therapy, which typically may only be one hour a day. In most cases, it is only during this time period of occupational or physical therapy that the patient is properly exercising the necessary muscles in order to recuperate from the disease, injury or disability so that the patient can regain use of the affected limb or extremity. Therefore, it would be desirable in the present invention to increase the amount of time that a patient spends in therapeutic movements of the affected limb. In addition, it is desirable in the present invention to provide a patient with the ability to continue therapeutic movements throughout the day, even after leaving the supervision of the physical therapist, and more particularly, to have such therapeutic movement occur in response to normal every day activities or movements of a non-affected extremity.

SUMMARY OF THE INVENTION

The present invention of a dynamic sling or harness is an orthotic device which promotes glenohumeral joint integrity, normalization of muscular tone, and movement for patients with hemiparesis and hemiplegia following central nervous system dysfunction. The dynamic sling provides therapeutic benefit and aids patients with improved joint positioning through its dynamic and continuous mechanisms. The patient will be able to provide continuous and intermittent joint approximation and proprioceptive sensory input to the hemiparetic or hemiplegic shoulder while wearing the dynamic sling. The dynamic sling is specifically appropriate for patients who present with glenohumeral sublexations. In addition, the unique design of the dynamic sling will further facilitate a posterior pull. This is beneficial as many of the glenohumeral sublexations are anterior as well as lateral.

Movement of the affected extremity is accomplished by active or passive shoulder flexion and/or horizontal adduction of the non-affected extremity from approximately 5° to 90°. Specifically, a cuff is worn on the non-affected extremity which attaches via webbing to a cable. Movement of the non-affected extremity activates a small and effective pull of approximately ¼" to ½" of the cable, which courses over a shoulder pad and through a cable guide attached to the shoulder pad by hook and loop material means, such as VELCRO. The cable eventually terminates onto a buckle which is attached by webbing to a neoprene cuff on the affected extremity.

Shoulder flexion and horizontal adduction are two of the most frequent movements performed with the functional, nonaffected upper extremity, which is one reason for the successful facilitation of joint approximation and proprioceptive input for a hemiplegic shoulder. In addition, joint approximation and proprioceptive input are treatments of choice for a hemiplegic shoulder, therefore, continuous, self treatment with a dynamic sling assists with expediting treatment benefits, as well as cost containment for a hemiplegic patient.

The cuff for the non-affected extremity can be constructed of AQUAPLAST, or other suitable low temperature plastic, in a generally rectangular shape having loop material connected to one side adjacent one end thereof and hook material connected to an opposite side adjacent an opposite end thereof for adjustably forming a cylinder of variable diameter. Preferably, a strap or webbing is connected to an external surface of the formed cylinder to provide means for securing the cylinder in a desired diametrical dimension. Once sized, the semi-rigid cuff can be slipped on the patient's non-affected arm, similar to a bracelet, to allow a patient to self-dress with the dynamic sling or harness.

One end of a connecting or attachment means is connected to the non-affected extremity cuff. This connection may be formed as a section of webbing riveted to the non-affected extremity cuff. The webbing portion of the connection means can include a temporary buckle to provide a length adjusting mechanism for the connection means. Typically, once properly sized this buckle can be removed and the webbing sewn at the appropriate length adjustment to eliminate any source of discomfort that may be present when the buckle moves across the back and shoulder area of a patient.

The webbing portion of the connection means opposite the non-affected extremity cuff can include a first hook buckle connected to the webbing. The first hook buckle is also connected to a second hook buckle through a length of cable.

The affected limb cuff can be formed of neoprene, or other suitable pliable material, in a generally rectangular form having loop material connected to one surface adjacent one end thereof and hook material connected to an opposite surface adjacent an opposite end thereof for forming generally cylindrical cuff of adjustable diameter. In the preferred embodiment, the connecting means for the affected cuff can include webbing connected to opposing sides of the cylindrical neoprene cuff, by means such as sewing. The webbing may include an adjustable buckle allowing lengthening and shortening of the length of webbing for proper sizing to the patient depending on the diameter of the arm or other affected extremity. The second hook buckle is connected to the webbing for attaching the two cuffs to one another. The neoprene cuff with hook and loop material allows the patient to attach the cuff to the affected extremity without too much difficulty.

The cable of the connection means passes through a cable guide riveted to an adjustable guide base. Hook material, is connected to the bottom of the cable guide base. Shoulder padding is provided, and the base can be constructed of a KYDEX material, or other suitable low temperature plastic. The top surface of the shoulder padding may include an area of loop material. The loop material area is provided for interconnection with the hook material on the bottom of the cable guide base. When properly fitted to a patient the hook and loop can be replaced with permanent housing cable guide which can be riveted directly to the KYDEX or other low temperature plastic. Once properly fitted, the cable does not compress the joint in a rest position, where the arms are straight down from the shoulder sockets. Movement of the active or non-affected extremity acts through the cable to continuously compress and approximate the affected joint, such as compression and approximation of the head of the affected humerus into the glenoid fossa.

Other objects, advantages and applications of the present invention will become apparent to those skilled in the art when the following description of the best mode contemplated for practicing the invention is read in conjunction with the accompanying drawings.

BRIEF DESCRIPTION OF THE DRAWINGS

The description herein makes reference to the accompanying drawings wherein like reference numerals refer to like parts throughout the several views, and wherein.

DESCRIPTION OF THE PREFERRED EMBODIMENT

Figure 1:
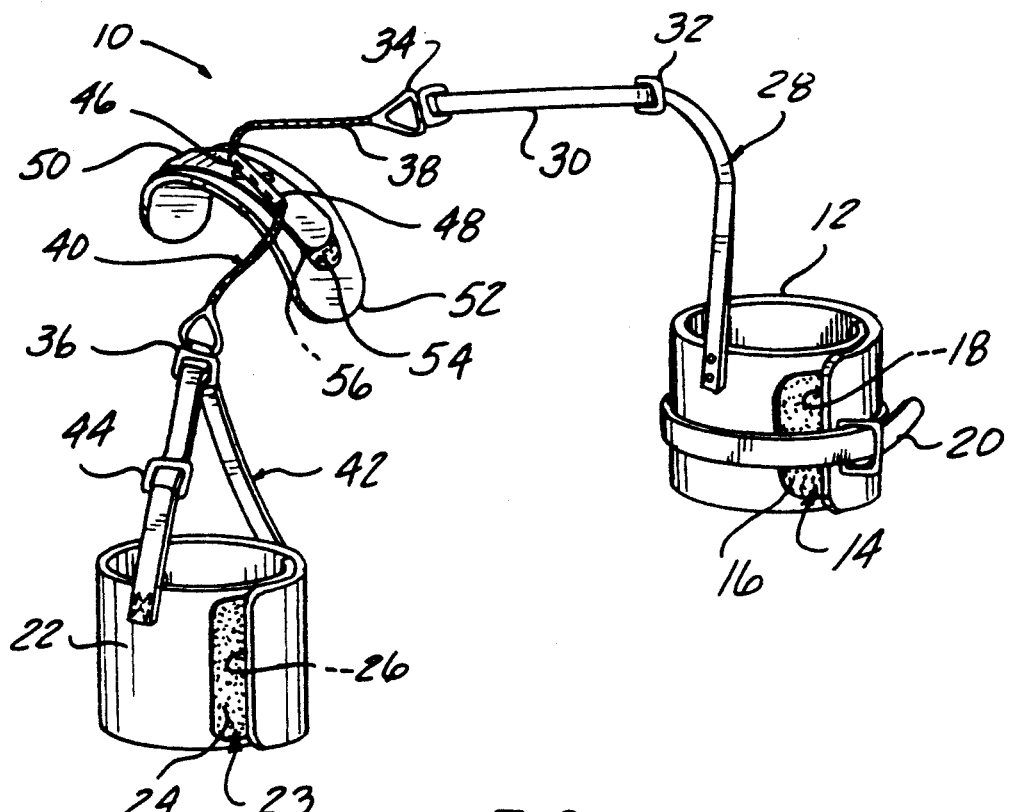
FIG. 1 is a perspective view of a dynamic sling according to the present invention.

A dynamic sling, generally designated as numeral 10, is shown in perspective view in FIG. 1. The dynamic sling or harness 10 includes a first cuff 12 adapted to engage a non-affected extremity. The first cuff 12 preferably is constructed of AQUAPLAST or other suitable low temperature plastic. The first cuff 12 is formed in a generally rectangular shape having adjustable fastening means 14 connected to the first cuff 12 for holding the rectangular material in end to end or overlapping end configuration to define a generally cylindrical shaped cuff having a diameter of adjustable dimension. The adjustable fastening means 14 can include loop material 16, such as VELCRO connected to one surface of the rectangular material adjacent one end, and a section of hook material 18, such as VELCRO, connected to an opposite surface of the rectangular material adjacent an opposite end for overlapping hook and loop material engagement to hold the opposing ends of the rectangular material adjacent to one another forming a generally cylindrical first cuff of adjustable diameter. In addition, or alternatively, the adjustable fastening means 14 may include a strap or webbing 20 connected to an external surface of the first cuff 12 having a buckle, clasp or hook and loop material closure to hold the first cuff 12 in position with a diameter sized to fit the particular patient. Once sized, the semi-rigid first cuff 12 can be slipped onto the patient's non-affected arm, similar to a bracelet, to allow a patient to self-dress while using the dynamic sling 10.

A second cuff 22 adapted to engage the affected extremity can be constructed of NEOPRENE, or other suitable pliable material, in a generally rectangular shape having adjustable fastening means 23 connected to the second cuff 22 for holding the rectangular material in end to end or overlapping end configuration to form a generally cylindrical shaped cuff having a diameter of variable dimension. The adjustable fastening means 23 can include loop material 24 connected to one surface of the rectangular material adjacent on end thereof and hook material 26 connected to an opposite surface adjacent an opposite end thereof for holding opposing ends of rectangular material adjacent to one another forming a generally cylindrical second cuff of adjustable diameter. The combination of the neoprene material and the hook and loop material closure for the second cuff 22 also assists in allowing the patient to self-dress while using the dynamic sling.

Elongated attachment means 28 connect the first cuff 12 to the second cuff 22. One end of the attachment means 28 is connected to the first cuff 12, while the other end of the attachment means is connected to the second cuff 22. The attachment means 28 connection to the first cuff 12 may be formed with a first portion 30 constructed of webbing connected to the first cuff 12 The connection of the webbing to the first cuff can be connected by any suitable means of attachment, such as by rivets. The first portion 30 of the attachment means 28 can also include a temporary buckle 32 to provide mean for adjusting a length of the attachment means 28 to fit a particular patient. Once properly sized, the temporary buckle 32 can be removed and the webbing sewn at the appropriate length adjustment to eliminate any source of discomfort that may be present when the temporary buckle 32 moves across the back and shoulder area of the patient. The end of the first portion 30 opposite from the first cuff 12 can include a first hook buckle 34 connected to the webbing. The first hook buckle 34 is also connected to a second hook buckle 36 through a length of cable 38. The first and second hook buckles, 34 and 36 respectively, and cable 38 defining a second portion 40 of the elongated attachment means 28. A third portion 42 of the elongated attachment means 28 can include webbing connected to opposing sides of the generally cylindrical second cuff 22. The connection of the webbing to the second cuff 22 can be accomplished in any suitable manner, such as by sewing. Preferably, an adjustable buckle 44 is provided in the webbing for adjusting the length of the webbing to allow proper sizing of the webbing depending on the diameter of the arm, or other affected extremity, or the distance D of sublexation. The second hook buckle 36 is connected to the third portion 42 webbing for attaching the first and second cuffs, 12 and 22 respectively, to one another. Constructing the second cuff 22 out of NEOPRENE, or other suitable pliable material, in combination with the hook and loop material closure makes it easier for the patient to attach the second cuff 22 to the affected extremity while dressing.

Figure 2:
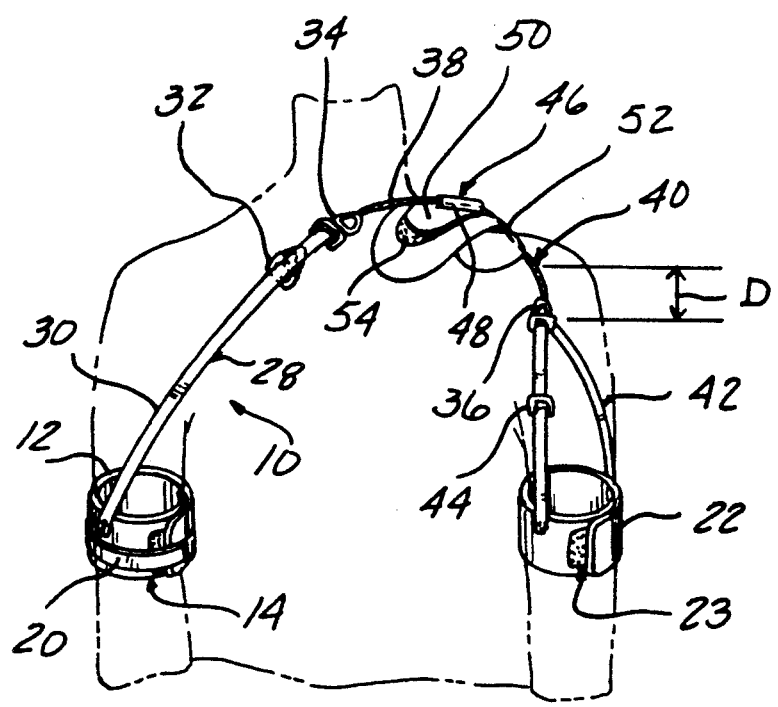
FIG. 2 is an elevational view showing a patient's torso with the dynamic sling positioned to treat an affected arm.

The elongated attachment means 28 passe through guide means 46 for properly positioning and transferring motion of cable 28 to the affected extremity to provide the desired therapeutic movement in response to movement of the non-affected extremity. Preferably, the guide means 46 includes a cable guide 48. The cable guide 48 encloses a portion of the cable 38 and has a guide base 50. The cable guide 48 and guide base 50 can be permanently or adjustably mounted to a padded, body engaging member 52. The padded, body engaging member 52 can be constructed of a KYDEX material, or other suitable low temperature plastic material. For purposes of illustration, the body-engaging member 52 can be a shoulder-engaging member 52 as shown in FIG. 2. In the preferred embodiment, the top surface of the shoulder-engaging member includes an area of loop material 54. The loop material area 54 is provided for interconnecting with a hook material area 56 connected to a bottom of the guide base 50 to allow the cable guide 48 to be adjustably positioned on the shoulder-engaging member 52 in order to obtain the desired therapeutic movement.

As shown in FIG. 2, when in use the dynamic sling 10 connects from the first cuff 12 disposed around a patient's nonaffected extremity, such as an arm, to a second cuff 22 attached to an affected extremity, such as a patient's other arm. When properly fitted to a patient, the cable does not compress the joint, or in other words does not decrease the distance D of sublexation while in a rest position where the patient's arms are straight down from the shoulder sockets. Movement of the nonaffected extremity, or active arm acts through the cable 38 to continuously compress and approximate the affected joint, such as compression and approximation of the head of the affected humerus to the glenoid fossa. Each of the first and second cuffs can be individually sized to fit the particular patient's dimensions. In addition, the elongated attachment means 28 can be sized to the particular patient using the temporary buckle 32. Further, the third portion 42 of the elongated attachment means 28 can be sized to accommodate the patient's dimensions as well as in order to obtain the desired therapeutic movement. In addition, the guide means 46 is preferably adjustable with respect to the padded, body-engaging member 52 in order to properly orientate the cable to the joint for different patient dimensions, and also to protect the patient from injury which might be caused by movement of the cable over the pressure bearing surface area of the patient between the first and second cuffs, in this particular instance the shoulder area of the patient. Movement of the active arm, particularly horizontal adduction, acts through the cable 38 to continuously compress and approximate the head of the affected humerus into the glenoid fossa.

It has been found that the dynamic sling of the present invention greatly accelerates the recovery process in comparison to patients not using the dynamic sling. It is believed that the rapid acceleration in recuperation is due to virtually continuous therapeutic movement imparted to the affected joint by the patient's movement of the active arm.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

I claim:

1. A dynamic sling for providing a patient with therapeutic movement including joint approximation and proprioceptive input for an affected shoulder joint, the dynamic sling comprising:
   first cuff means for attachment to a non-affected humeral extremity of said patient adjacent a non-affected shoulder joint;
   second cuff means for attachment to an affected humeral extremity of said patient adjacent an affected shoulder joint; and
   elongated attachment means for connecting said first and second cuff means to one another and for transferring movement from said non-affected humeral extremity to said affected humeral extremity during normal movement of the non-affected humeral extremity of said patient, said attachment means connected to said first cuff means at one end and passing over an affected shoulder of said patient before connected to said second cuff means at an opposite end, and a guide means supported by a shoulder adjacent the affected shoulder joint and opposite from said first cuff means.

2. The dynamic sling of claim 1 wherein said guide means further comprises:
   a hollow guide member for enclosing a portion of said attachment means; and
   a padded, body-engaging member supporting the hollow guide member away from said patient.

3. The dynamic sling of claim 2 further comprising:
   means for connecting the hollow guide member to the padded, body-engaging member.

4. The dynamic sling of claim 1 wherein said first cuff means further comprises:
   a rectangular, semi-rigid member having an elongated length of greater dimension than a width, the length of sufficient dimension to encircle the non-affected humeral extremity of said patient; and
   adjustable closure means for forming the rectangular, semi-rigid member into a generally cylindrical shape with a diameter of variable dimension.

5. The dynamic sling of claim 4 wherein said adjustable closure means further comprises:
   a first area of hook material connected to a first surface of aid rectangular member adjacent one end thereof; and
   a second area of loop material connected to a second surface of said rectangular member opposite from said first surface and adjacent a second end opposite said first end, such that said area of hook material is brought into overlapping engagement with said second area of loop material when said rectangular member is formed into a generally cylindrical shape having overlapping first and second ends.

6. The dynamic sling of claim 5 further comprising:
   securing means for holding the rectangular member in a desired cylindrical configuration having a diameter of preselected dimension.

7. The dynamic sling of claim 6 wherein said securing means further comprises:
   a strap connected to the rectangular member for encircling an external periphery of the rectangular member when in said desired cylindrical configuration, the strap including hook and loop material connected to an outwardly facing surface of the strap, and a D-ring attached adjacent a base of the strap, such that the strap can be positioned encircling the rectangular member and threaded through the D-ring and folded over to interconnect the hook and loop material.

8. The dynamic sling of claim 1 wherein said second cuff means further comprises:
   a rectangular, pliable member having an elongated length of greater dimension than a width, the length of sufficient size to encircle an affected humeral extremity of said patient; and
   adjustable closure means for holding the rectangular, pliable member in a position generally encircling the affected humeral extremity of said patient.

9. The dynamic sling of claim 8 wherein said adjustable closure means further comprises:
   a first area of hook material connected to a first surface of said rectangular, pliable member adjacent a first end; and
   a second area of loop material connected to a second surface of said rectangular, pliable member opposite from said first surface and adjacent a second end opposite said first end, such that said rectangular, pliable member can be disposed in a generally cylindrical configuration with said first and second ends overlapping one another with said first area of hook material overlapping said second area of loop material to hold the rectangular, pliable member in a desired position.

10. The dynamic sling of claim 1 wherein said attachment means further comprises:
    a first portion connected to said first cuff means;
    a second portion having first and second ends, a first end connected to said first portion; and
    a third portion connected to said second cuff means and connected to said second end of said second portion for transferring motion from said non-affected humeral extremity of said patient to said affected humeral extremity of said patient.

11. The dynamic sling of claim 10 wherein said first portion further comprises:
    a temporary buckle disposed in the first portion for allowing adjustment of the length of the first portion for said patient to be fitted.

12. The dynamic sling of claim 10 wherein said third portion further comprises:
    said third portion connected to said second cuff means in at least two locations spaced apart from one another; and
    adjustable buckle means for adjusting a length of the third portion.

13. A dynamic sling for providing a patient with therapeutic movement including joint approximation and proprioceptive input for an affected shoulder joint, the dynamic sling comprising:
- first cuff means for attachment to a non-affected humeral extremity of said patient adjacent a non-affected shoulder joint, the first cuff means including a rectangular, semi-rigid member having an elongated length of greater dimension than a width, the length of sufficient dimension to encircle the non-affected humeral extremity of said patient, and adjustable closure means for forming the rectangular, semi-rigid member into a generally cylindrical shape with a diameter of variable dimension;
- second cuff means for attachment to an affected humeral extremity of said patient adjacent an affected shoulder joint, the second cuff means including a rectangular, pliable member having an elongated length of greater dimension than a width, the length of sufficient size to encircle an affected humeral extremity of said patient, and adjustable closure means for forming the rectangular, pliable member into a generally cylindrical shape with a diameter of variable dimension;
- elongated attachment means for connecting said first and second cuff means to one another and for transferring movement from said non-affected humeral extremity to said affected humeral extremity during normal movement of the non-affected humeral extremity of said patient; and
- guide means supported by a shoulder portion of said patient for guiding at least a portion of said attachment means in longitudinal movement between said first and second cuff means.

14. The dynamic sling of claim 13 wherein said guide means further comprises:
- a hollow guide member for enclosing a portion of said attachment means; and
- a padded, body-engaging member supporting the hollow guide member away from said patient.

15. The dynamic sling of claim 14 further comprising: means for connecting the hollow guide member to the padded, body-engaging member.

16. The dynamic sling of claim 13 wherein said attachment means further comprises:
- a first portion connected to said first cuff means;
- a second portion having first and second ends, a first end connected to said first portion; and
- a third portion connected to said second cuff means and connected to said second end of said second portion for transferring motion from said non-affected humeral extremity of said patient to said affected humeral extremity of said patient.

17. The dynamic sling of claim 16 wherein said first portion further comprises:
- a temporary buckle disposed in the first portion for allowing adjustment of the length of the first portion for said patient to be fitted.

18. The dynamic sling of claim 16 wherein said third portion further comprises:
- said third portion connected to said second cuff means in at least two locations spaced apart from one another; and
- adjustable buckle means for adjusting a length of the third portion.

19. A dynamic sling for providing a patient with therapeutic movement including joint approximation and proprioceptive input for an affected shoulder joint, the dynamic sling comprising:
- a first cuff for attachment to a non-affected humeral extremity of said patient adjacent a non-affected shoulder joint, the first cuff having a rectangular, semi-rigid member with an elongated length of greater dimension than a width, the length of sufficient dimension to encircle the non-affected humeral extremity of said patient and an adjustable closure for forming the rectangular, semi-rigid member into a generally cylindrical shape with a diameter of variable dimension, the adjustable enclosure having a first area of hook material connected to a first surface of said rectangular member adjacent one end thereof and a second area of loop material connected to a second surface of said rectangular member opposite from said first surface and adjacent a second end opposite said first end, such that said area of hook material is brought into overlapping engagement with said second area of loop material when said rectangular member is formed into a generally cylindrical shape having overlapping first and second ends, a strap for holding the rectangular member in a desired cylindrical configuration having a diameter of preselected dimension, the strap connected to the rectangular member for encircling an external periphery of the rectangular member when in said desired cylindrical configuration, the strap including hook and loop material connected to an outwardly facing surface of the strap, and a D-ring attached adjacent a base of the strap, such that the strap can be positioned encircling the rectangular member and threaded through the D-ring and folded over to interconnect the hook and loop material;
- a second cuff for attachment to an affected humeral extremity of said patient adjacent an affected shoulder joint, the second cuff having a rectangular, pliable member with an elongated length of greater dimension than a width, the length of sufficient size to encircle an affected humeral extremity of said patient and an adjustable closure for holding the rectangular, pliable member in a position generally encircling the affected humeral extremity of said patient, the adjustable closure having a first area of hook material connected to a first surface of said rectangular, pliable member adjacent a first end and a second area of loop material connected to a second surface of said rectangular, pliable member opposite from said first surface and adjacent a second end opposite said first end, such that said rectangular, pliable member can be disposed in a generally cylindrical configuration with said first and second ends overlapping one another with said first area of hook material overlapping said second area of loop material to hold the rectangular, pliable member in a desired position;
- an elongated attachment for connecting said first and second cuffs to one another and for transferring movement from said non-affected humeral extremity to said affected humeral extremity during normal movement to the non-affected humeral extremity of said patient, said attachment connected to said first cuff at one end and passing over an affected shoulder of said patient before connecting to said second cuff at an opposite end, the attachment connected to said second cuff in at least two locations spaced apart from one another; and
- a guide for enclosing and for guiding longitudinal movement of at least a portion of said attachment between said first and second cuffs, the guide including a hollow guide member for enclosing a portion of said attachment and a padded, body-engaging member supporting the hollow guide member away from said patient, the body-engaging member disposed on top of and adjacent to the affected shoulder of the patient, the hollow guide member connected to the padded, body-engaging member, such that shoulder flexion and horizontal adduction of the non-affected humeral extremity moves the attachment longitudinally within the hollow guide member and across the body-engaging member protecting the affected shoulder of the patient to dynamically cause joint approximation and proprioceptive input for the affected humeral extremity in response to normal movements of the non-affected humeral extremity.

* * * * *